US00PP24710P3

(12) United States Plant Patent
Schoone

(10) Patent No.: US PP24,710 P3
(45) Date of Patent: Jul. 29, 2014

(54) ***PHALAENOPSIS* ORCHID PLANT NAMED 'WINTERDAY'**

(50) Latin Name: ***Phalaenopsis* hybrid**
Varietal Denomination: Winterday

(75) Inventor: René Schoone, Assendelft (NL)

(73) Assignee: Floricultura, Heemskerk (NL)

( * ) Notice: Subject to any disclaimer, the term of this patent is extended or adjusted under 35 U.S.C. 154(b) by 114 days.

(21) Appl. No.: 13/506,391

(22) Filed: Apr. 17, 2012

(65) Prior Publication Data

US 2012/0272414 P1 Oct. 25, 2012

Related U.S. Application Data

(60) Provisional application No. 61/478,803, filed on Apr. 25, 2011.

(30) Foreign Application Priority Data

Apr. 27, 2011 (NL) ..... PBR OPS792

(51) Int. Cl.
*A01H 5/00* (2006.01)
*A01H 5/02* (2006.01)

(52) U.S. Cl.
CPC ..... *A01H 5/02* (2013.01)
USPC ..... Plt./311

(58) Field of Classification Search
CPC ..... A01H 5/00; A01H 5/02
USPC ..... Plt./311
See application file for complete search history.

(56) References Cited

U.S. PATENT DOCUMENTS

2012/0272419 P1 * 10/2012 Schoone ..... Plt./311
2012/0272423 P1 * 10/2012 Schoone ..... Plt./311
2013/0125277 P1 * 5/2013 Schoone ..... Plt./311

* cited by examiner

*Primary Examiner* — Wendy C Haas
(74) *Attorney, Agent, or Firm* — Foley & Lardner LLP

(57) ABSTRACT

A new and distinct *Phalaenopsis* plant named 'Winterday' particularly characterized by flowers which are white; within the labellum some yellow and purple; plants which may be propagated economically and uniformly using tissue culture; plants which produce more than one inflorescence; long and sturdy inflorescences; and relatively short, dark-green foliage.

3 Drawing Sheets

Latin name of the genus and species of the plant claimed: *Phalaenopsis* hybrid.

Variety denomination: 'Winterday'.

BACKGROUND OF THE INVENTION

The present invention relates to a new and distinct cultivar of *Phalaenopsis* plant, botanically known as *Phalaenopsis* of the Orchidaceae family, and hereinafter referred to by the cultivar name 'Winterday'.

*Phalaenopsis* comprises a genus of about 55 species of herbaceous perennials many of which, or the hybrids thereof, are suitable for cultivation in the home or greenhouse. *Phalaenopsis* is predominantly epiphytic or rock-dwelling, and is native to tropical Asia, the Malay Archipelago, and Oceania. The species typically has 2-ranked, fleshy, oblong or elliptic leaves affixed to a short central stem (monopodial growth), which vary in size from 5 to 8 inches to over 2 feet. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes, often with many showy flowers which open in succession beginning with the lowermost. The flowers possess three sepals and three petals; the lateral ones being alike. The lowermost petal, called the labellum, is three-lobed and is often more brightly-colored than the other flower segments. Flower colors include various shades of pink, white, yellow and red-brown.

*Phalaenopsis* orchids are typically propagated from seeds. Asexual propagation of *Phalaenopsis* is often done from off-shoots which frequently arise from the lower bracts of the inflorescence. The resulting plants are detached from the mother plant and may be planted in a suitable substrate.

The new *Phalaenopsis* 'Winterday' is a product of a controlled breeding program conducted by the inventors, René Schoone, in Strengweg, Heemskerk, The Netherlands. The objective of the breeding program was to develop a new *Phalaenopsis* cultivar particularly characterized by its attractive and unique colored flowers, economical propagation via tissue culture, rapid growth, and a plant dimension suitable for packaging and shipping to the market.

The new *Phalaenopsis* 'Winterday' originated from a cross made by the inventor in 1998 in Strengweg, Heemskerk, The Netherlands. The female or seed parent is the *Phalaenopsis* cultivar designated 'Sogo Yukidian', unpatented. The male or pollen parent is the *Phalaenopsis* cultivar designated 'World Class', unpatented. The new *Phalaenopsis* 'Winterday' was discovered and selected by the inventor as a single flowering plant within the progeny of the stated cross in a controlled environment in 2006 in Strengweg, Heemskerk, The Netherlands.

Asexual reproduction of the new *Phalaenopsis* cultivar by tissue culture was first performed in November, 2006 in Cieweg 13, Heemskerk, The Netherlands, and has demonstrated that the combination of characteristics as herein disclosed for the new cultivar are firmly fixed and retained through successive generations of asexual reproduction. The new cultivar asexually reproduces true-to-type.

BRIEF DESCRIPTION OF THE INVENTION

The following traits have been repeatedly observed and are determined to be unique characteristics of 'Winterday', which in combination distinguish this *Phalaenopsis* as a new and distinct cultivar:

1. flowers which are white; within the labellum some yellow and purple;
2. plant produces more than one inflorescence;
3. plants may be propagated economically and uniformly using tissue culture;
4. inflorescence is long and sturdy; and
5. relatively short, dark-green foliage.

In comparison with the parental cultivars of 'Winterday', the female parent 'Sogo Yukidian' has large white flowers, about 12 cm in size, the male parent 'World Class' has white flowers, about 10 cm in size, whereas the flowers of 'Winterday' are about 11 cm in size.

Presently, the most commercially similar cultivars to 'Winterday' are the parent cultivars, 'Sogo Yukidian' and 'World Class', to which a comparison has already been provided above.

BRIEF DESCRIPTION OF THE PHOTOGRAPHS

The accompanying photographs illustrate the overall appearance of the new *Phalaenopsis* 'Winterday' showing the colors as true as is reasonably possible with colored reproductions of this type. Colors in the photographs may differ slightly from the color values cited in the detailed botanical description, which accurately describe the color of 'Winterday'.

DETAILED BOTANICAL DESCRIPTION

Figure 1:
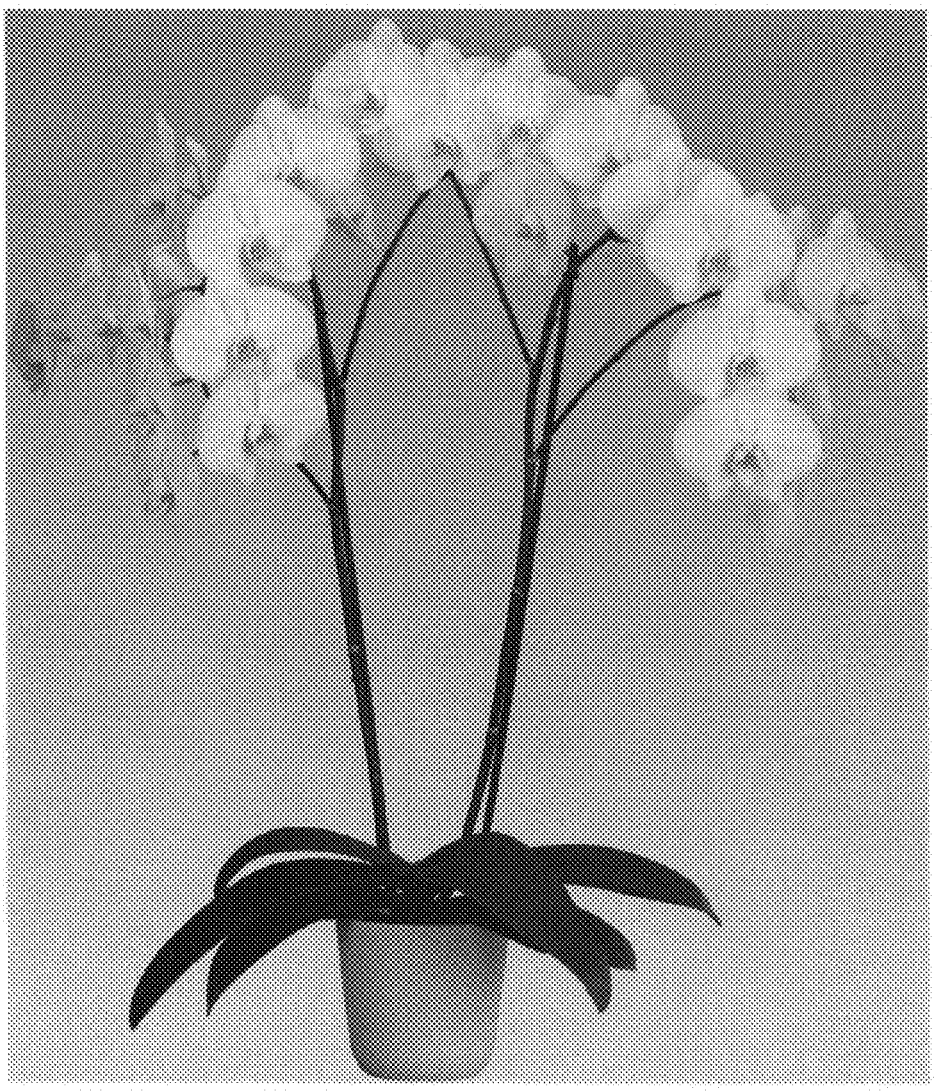
FIG. 1 shows a side view perspective of a typical flowering plant of 'Winterday' in a 12 cm pot, at 16 months of age.

The new *Phalaenopsis* cultivar 'Winterday' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'Winterday' as grown in a greenhouse in Strengweg, Heemskerk, The Netherlands, under conditions which closely approximate those generally used in commercial practice. Initially, the ideal temperature to grow plants of 'Winterday' is 27° C. during the day and at night. Then, during the flowering phase of 'Winterday', the ideal growing temperature is 20-22° C. during the day and 18° C. at night. Light levels for growing 'Winterday' are a minimum of 5,000 lux and a maximum of 10,000 lux. A balanced fertilizer with level of 200 ppm N, 87 ppm P, 168 ppm K is applied. Duration of growth of 'Winterday' from potting size is between 10 and 14 months.

Color references are made to The Royal Horticultural Society Colour Chart (R.H.S.), 2007 edition, except where general colors of ordinary significance are used. Color values were taken under daylight conditions at approximately noon in Zaandammerweg, Assendelft, The Netherlands. The age of the 'Winterday' plants described is 12 months after potting.

Classification:

*Botanical.*—*Phalaenopsis* hybrid.

Parentage:

*Female or seed parent.*—*Phalaenopsis* cultivar designated 'Sogo Yukidian', unpatented.

*Male or pollen parent.*—*Phalaenopsis* cultivar designated 'World Class', unpatented.

Propagation:

*Type.*—Tissue culture.

*Rooting habit and description.*—Approximately 4 mm-7 mm wide and greyed/green in color (RHS 194A and RHS N189D); freely branching. It takes 12 weeks for plants growing in tissue culture to initiate roots.

Plant:

*Size at maturity.*—Height (from bottom of pot to the highest flower): about 75 cm. Spread: about 50 cm.

*Growth habit.*—Standard; green leaves (RHS N137A) and a relatively normal raceme.

*Vigor.*—Moderate.

*Crop time.*—Following asexual propagation, at about 26 weeks 2 leaves appear; at about 30 weeks 3-4 leaves appear; after a cold treatment of about 4-8 weeks at a temperature of about 19° C. about 2 racemes with flowers appear.

Foliage:

*Quantity per plant.*—About 6 to 8 leaves are produced before flowering.

*Arrangement and attachment.*—Half up/horizontal and on two sides.

*Overall shape of leaf.*—Oval, the tip is blunt and asymmetric.

*Texture (both surfaces).*—Smooth and leathery.

*Pubescence.*—None.

*Mature leaf length.*—About 10 to 25 cm.

*Mature leaf width.*—About 5 to 10 cm.

*Mature leaf thickness.*—About 2 mm.

*Mature leaf color.*—Upper side: green (RHS N137A). Under side: green (RHS 137B).

*Leaf base.*—Acute.

*Margin.*—Entire.

*Venation.*—Pattern: parallel. Color of midvein: upper side: green (RHS N137A). Under side: green (RHS 137B).

Raceme:

*Quantity per plant.*—About 1 to 2.

*Number of flowers per raceme.*—About 4 to 8.

*Length.*—About 75 cm to 85 cm.

*Diameter.*—About 5 mm.

*Strength.*—Strong.

*Aspect.*—Upright.

*Texture.*—Glabrous and smooth.

*Color.*—Green (RHS N137A) with green (RHS 137D).

*Internode.*—Length: about 30 to 40 mm.

Inflorescence description:

*Appearance.*—Upright to slightly pendant, racemose inflorescence with bilaterally symmetrical flowers that open in succession beginning with the lowermost flower.

*Buds*.—Height (from base to tip): about 15 mm to 25 mm. Diameter (at midpoint): about 15 mm to 25 mm. Shape: oval/egg-shaped. Color: yellow/green (RHS 145A and RHS 145B). Orientation: same orientation as the flowers (forward facing).

*Flowering time*.—For an untreated plant (flowering plant that has not undergone cold-treatment where the plant grows at a temperature of 18° C. to 19° C. for about 4 to 8 weeks after a period of about 30 weeks at a temperature of 25° C.), 2 racemes appear with about 16 to 20 flower buds and flowers per inflorescence. First flowers can be expected approximately 4 to 6 months after planting a plant with a leaf diameter of 3 to 5 cm. Flowers persistent.

*Flowering longevity*.—On the plant: about 4 to 6 months; lastingness of cut flowers: has not been observed.

*Fragrance*.—No fragrance.

Figure 2:
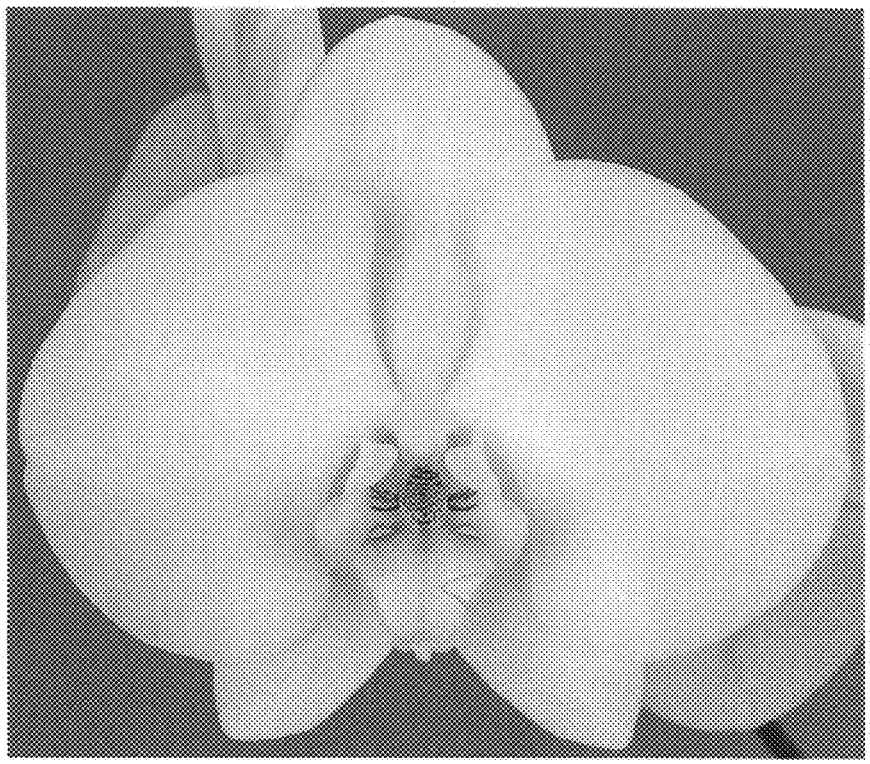
FIG. 2 shows a close-up view of the typical buds and flowers of 'Winterday'.
Figure 3:
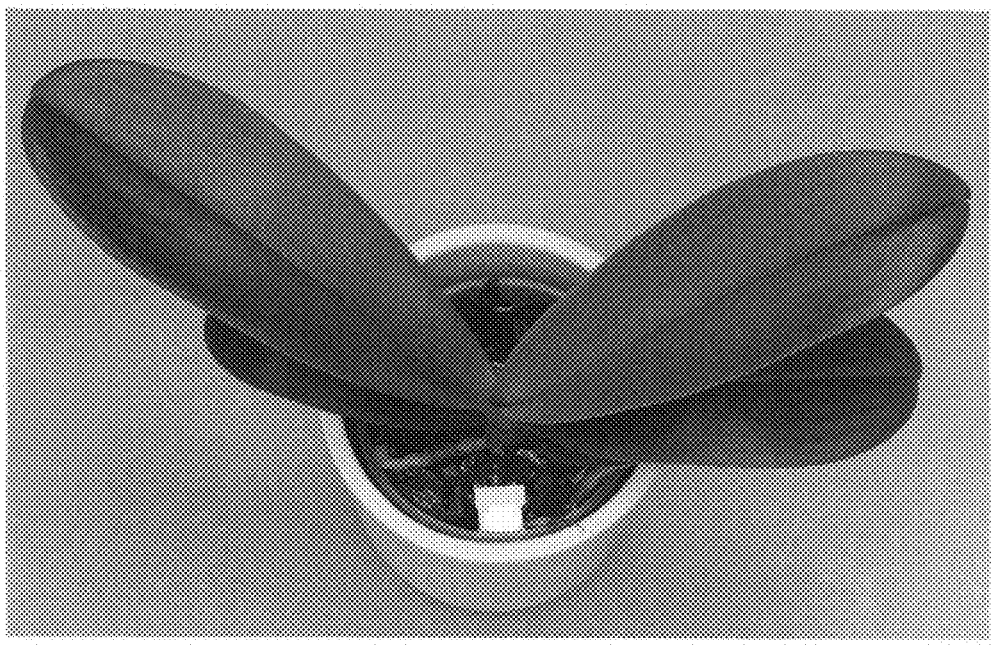
FIG. 3 shows a close-up view of the typical leaves of 'Winterday'.

*Flower*.—Rate of opening: Flowers fully opened about 2 to 3 days after petal and sepal separation. Orientation at opening: slanted upward and outward. Shape: Typical shape of *Phalaenopsis*; see FIG. 2. Size: Height of single bloom: about 95 mm. Diameter of single bloom: about 110 mm. Depth of tube: about 20 mm.

*Petals*.—Quantity and arrangement: three petals and three sepals that are trimerous, overlapping and arranged in 2 whorls. Petals are more pronounced than sepals. Arrangement: Inner whorl comprises 3 petals, 2 lateral petals and labellum. 2 lateral petals: Overall shape: broadly ovate and weakly cupped. Apex: oval. Margin: entire and weakly undulate. Base: broadly ovate. Length: about 67 mm. Width: about 50 mm. Texture: Upper surface: smooth and satiny. Under surface: smooth and satiny. Color (when fully opened): upper and under surface: white (RHS NN155D). Labellum: Overall shape: 3-lobed with 2 prominent callosities at central junction of the lateral lobes and base of the midlobe. Lateral lobes of labellum fold upward about the column; the midlobe extends forward and is terminated by 2 filiform appendages at the apex. Lateral lobes of the labellum are ovate in shape while the midlobe is triangular with a bump and a rib on it. Margin: entire and weakly undulate. Apex: oval. Length: about 28 mm. Width (not flattened): about 22 mm. Texture: Upper and under surface: smooth and satiny. Color (when fully opened): Main color of mid lobe and lateral lobes is white (RHS NN155C). The top edges of the mid lobe are purple-red (RHS 71A) and the top is yellow/green (RHS 1A). At the base of the lateral lobes are red/purple stripes (RHS 71A). The bottom edges are green/yellow (RHS 1A). Under surface: white (RHS NN155C). Mid lobe top edges are purple/red (RHS 71B) and yellow/green (RHS 1A). Lateral lobes bottom edges are green/yellow (RHS 1A) which runs into RHS 1C. Cirrhi: long (about 20 mm). Color: yellow (RHS 3B). Pestle (Callosities): Length: about 5 mm. Width (not flattened): about 7 mm. Color: yellow (RHS 3A) with red/purple stripes and spots (RHS 71A).

*Sepals*.—Arrangement: Outer whorl comprises 3 sepals. Overall shape: elliptical and weakly cupped. Margin: entire and weakly undulate. Length: about 50 mm. Width: about 30mm to 40 mm. Apex: oval. Lateral are little more pointy. Texture: Upper and under surface: smooth and satiny. Color (when fully opened): white (RHS NN155C) with at the lateral sepals a light haze of green/yellow (RHS 1C). Under surface: White (RHS NN155C) with a haze of green/yellow (RHS 1 C).

*Pedicel*.—Length: about 37 mm. Diameter: about 4 mm. Color: white (RHS NN155B) which runs into yellow/green (RHS 145B) and then into RHS 146C.

Reproductive organs:

*Arrangement*.—The stamens, style and stigmas are fused into a single, short structure called the column, possessing one terminal anther with pollen grains united into a pollinia, which are covered by an anther cap. The stigma is located under the column behind the pollinia. The ovary is inferior with three carpels present. The plant has not produced seed.

*Column*.—Length: about 12 mm. Diameter: about 7 mm. Color: white (RHS NN155C).

*Pollinia*.—Quantity: Two. Size: about 1 mm. Color: orange (RHS N25A).

*Ovary*.—Length: about 7 mm. Diameter: about 7 mm. Color: white (RHS NN155C).

Disease/pest resistance/susceptibility: No specific resistance or susceptibility observed.

Temperature tolerance: Tolerant to a low temperature of about 15° C. and to a high temperature about 30° C.

What is claimed is:

1. A new and distinct *Phalaenopsis* plant named 'Winterday', as illustrated and described herein.

* * * * *